(12) United States Patent
Ko et al.

(10) Patent No.: US 8,753,492 B2
(45) Date of Patent: Jun. 17, 2014

(54) METHOD FOR ENHANCING CURRENT THROUGHPUT IN AN ELECTROCHEMICAL SYSTEM

(75) Inventors: Sung Hee Ko, Nan-Gu (KR); Sung Jae Kim, Melrose, MA (US); Jongyoon Han, Bedford, MA (US); HiongYap Gan, Revere, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 138 days.

(21) Appl. No.: 13/162,911

(22) Filed: Jun. 17, 2011

(65) Prior Publication Data

US 2012/0247979 A1    Oct. 4, 2012

Related U.S. Application Data

(60) Provisional application No. 61/355,703, filed on Jun. 17, 2010.

(51) Int. Cl.
*G01N 27/327* (2006.01)
*H01M 8/10* (2006.01)

(52) U.S. Cl.
USPC ..................... 204/403.01; 429/491

(58) Field of Classification Search
USPC ............. 429/491–494; 204/403.01–403.15, 204/416–419, 409–412
See application file for complete search history.

(56) References Cited

U.S. PATENT DOCUMENTS

| | | | |
|---|---|---|---|
| 5,338,429 A * | 8/1994 | Jolson et al. | 204/415 |
| 6,413,663 B1 * | 7/2002 | Mercuri | 429/483 |
| 6,960,402 B2 * | 11/2005 | Yazici et al. | 429/481 |
| 8,303,800 B2 * | 11/2012 | Fukuda et al. | 205/775 |
| 2006/0255464 A1 | 11/2006 | D'Arrigo et al. | |
| 2007/0020496 A1 | 1/2007 | Pelton et al. | |
| 2007/0148527 A1 | 6/2007 | Siciliano et al. | |
| 2008/0248343 A1 * | 10/2008 | Markoski et al. | 429/15 |

FOREIGN PATENT DOCUMENTS

| | | | | |
|---|---|---|---|---|
| WO | WO-2009/031375 A1 * | 12/2009 | | G01N 27/30 |
| WO | WO 2010/148198 A1 * | 12/2010 | | H01M 8/00 |

OTHER PUBLICATIONS

Ko, S.H., et al., "Limiting Convection Near Ion Selective Nanojunction Leads to the Removal of Limiting Current Behavior," 13th Annual International Conference on Miniaturized Systems for Chemistry and Life Sciences, pp. 168-170 (Nov. 5, 2009).
Cheow, et al., "Increasing the Sensitivity of Enzyme-Linked Immunosorbent Assay Using Multiplexed Electrokinetic Concentrator," Analytical Chemistry: 82, pp. 3383-3388 (Apr. 2010).
Kim, et al., "Self-Sealed Vertical Polymeric Nanoporous-Junctions for High-Throughput Nanofluidic Applications," Analytical Chemistry: 80, pp. 3507-3511 (May 2008).

* cited by examiner

*Primary Examiner* — Alex Noguerola
(74) *Attorney, Agent, or Firm* — Elmore Patent Law Group, P.C.; Carolyn S. Elmore, Esq.; Roy P. Isaac

(57) ABSTRACT

An electrochemical system with reduced limiting-current behavior is disclosed. The electrochemical system is useful for fuel cells and bio-sensors. In part, the invention relates a method of reducing or eliminating limiting-current behavior in the operation electrochemical systems, in particular those with ion-selective membrane or electrochemical electrodes, by spatially reducing the convection near the membrane or the electrode. The invention further relates to electrochemical systems in which micropores, microarrays or pillar arrays are used to reduce convection in comparison to conventional systems without microarrays, micropores or pillar arrays.

31 Claims, 20 Drawing Sheets

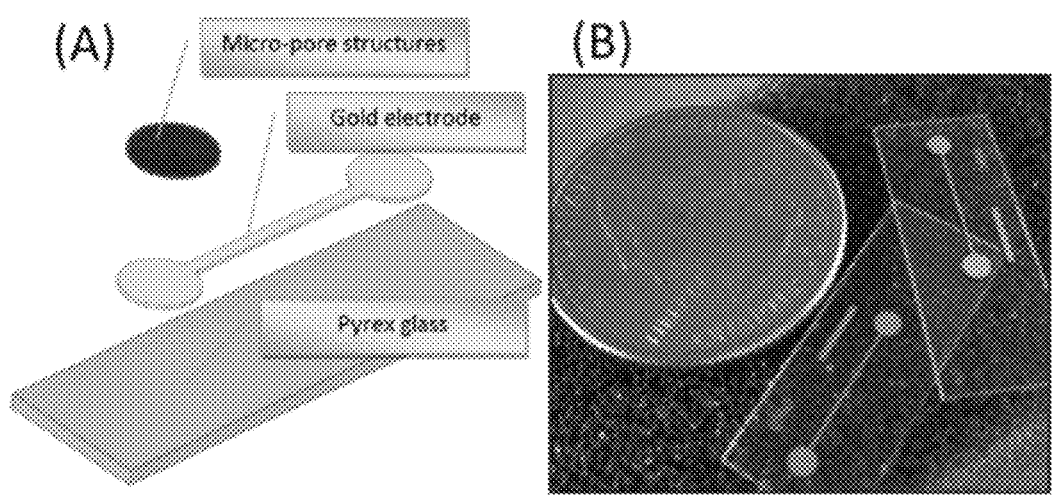
FIG. 8A-B

FIG. 13A-C

METHOD FOR ENHANCING CURRENT THROUGHPUT IN AN ELECTROCHEMICAL SYSTEM

RELATED APPLICATION

This application claims the benefit of U.S. Provisional Application No. 61/355,703 filed Jun. 17, 2010. The entire teachings of the above-referenced application are incorporated herein by reference.

GOVERNMENT SUPPORT

This invention was made with government support under Grant No. NSF0854026 awarded by the National Science Foundation. The government has certain rights in this invention.

BACKGROUND OF THE INVENTION

Ion concentration polarization (ICP) is a fundamental electrochemical phenomenon that describes the mismatch of charge carriers at the nanoporous membrane or nanochannel interface (Rubinstein, et al., *Journal of Chemical Society Faraday Transactions II*, 75, 231 (1979); Holtzel, et al., *Journal of Separation Science* 30, 1398 (2007)). Significant concentration gradient can be generated when ion current is transported through perm-selective membranes (nanochannels) or electrodes, altering the overall conduction properties of these electrochemical systems. Understanding ICP and related transport phenomena is important in many engineering fields such as bio-sensing, and fuel cells application. (Wang, et al., *Anal. Chem.*, 77, 4293 (2005); Wang, et al., *Lab Chip*, 8, 392 (2008); Song, et al., *Power Sources*, 183, 674 (2008)). Classical theory of ICP, originally developed by Nemst in 1904, predicts that there will be a maximum current allowed through the perm-selective membrane (limiting current behavior), because ion concentration in the anodic side of the membrane reaches near zero. At this point (called as limiting current condition) no further increase in ion current through membrane is possible even if the bias is further increased. (Probstein, et al., Physicochemical Hydrodynamics: An Introduction (Wiley-Interscience, 1994)). However, in reality, significant over-limiting current can always be observed experimentally in most perm-selective membranes. The detailed physical mechanism of over-limiting current has been in debate since as early as 1979. (Rubinstein, et al., supra). Overlimiting current is often associated with water dissociation at the vicinity of the membrane, but recently, Kim, et al. experimentally confirmed the existence of strong convection of fluid layer near the membrane, in direct coincidence with the formation of depletion zone (diffusion layer) as well as the classic over-limiting current behavior. (Strathmann, et al., *J. Membr. Sci.*, 125, 123 (1997); Kim, et al., *Phys. Rev. Lett.*, 99, 044501 (2007)). The importance of fluid flow in ICP and limiting current behavior is now well established, both theoretically and experimentally. (Rubinstein, et al., *Phys. Rev. E*, 62, 2238 (2000); Pundik, et al., *Phys. Rev. E*, 72 (2005); Rubinstein, et al., *Phys. Rev. Lett.*, 101, 236101 (2008)).

Electrochemical systems using microfluidic technology are becoming important for a variety of fields including fuel cells and biosensors. (U.S. Patent Publications 20090242406, 20080253929, 20060292407 and U.S. Pat. Nos. 6,444,339 and 7,381,858).

In most electrochemical membrane applications, limiting current behavior is the source of concentration over-potential, which significantly limits the ion/chemical transport through the membrane. As such, a need exists to develop a method for effectively reducing or preventing limiting current behavior. A reduction in limiting current behavior would potentially enhance the electrochemical membrane performance significantly.

SUMMARY OF THE INVENTION

In part, the invention relates to a method of reducing or eliminating limiting-current behavior in the operation of electrochemical systems, in particular those with ion-selective membrane or electrochemical electrodes, by spatially reducing the convection near the membrane or the electrode. The invention further relates to electrochemical systems in which micropore arrays, microarrays or pillar arrays are used to reduce convection in comparison to conventional systems without microarrays, micropore arrays, or pillar arrays.

In one embodiment, the invention relates to an electrochemical system comprising a substrate, a plurality of microchannels fabricated onto said substrate, and a nanojunction connecting at least two of said microchannels wherein at least a part of said substrate contains a microarray, microarray or a pillar array. In certain embodiments, the substrate contains a micropore array or a pillar array. In certain additional embodiments, the substrate contains a pillar array at the anodic side of the nanojunction. In yet another aspect, the substrate contains a micropore array at the anodic side of the nanojunction. The system can be one in which a microchannel can contain a fluid wherein when a current is applied, convection currents near said nanojunction is reduced when compared to convection currents near a nanojunction of same type of electrochemical system without a pillar array or micropore array. The system can further comprise an ion-selective membrane between said microchannels.

In additional aspects, the invention relates to a method of reducing limiting current behavior across an ion-selective membrane in an electrochemical system comprising providing a fabricated non-planar structure on at least one side of the membrane and wherein the electrochemical system comprises a substrate, wherein said substrate comprises a microchannel. Convection near said membrane can be reduced in comparison to having planar structures on both sides of the membrane. In one embodiment, the non-planar structure is a micro-array, a pillar array, or a micropore array. In additional aspects, the microchannel is curved in shape, for example, the microchannel can be parabolic in shape. In some embodiments, the microchannel has a locus in proximity to a nanochannel.

In certain additional aspects, the invention is directed to a method of reducing an ion depletion region in an electrochemical system comprising providing a fabricated non-planar structure on at least one side of an ion-selective membrane wherein said non-planar structure reduces convection near said membrane.

In yet another aspect, the invention is an electrochemical system comprising a substrate, a plurality of fluidic channels fabricated on said substrate, wherein at least two separate fluidic channels are connected by a junction, wherein at least one part of said substrate contains a pillar array. In one embodiment, the fluidic channels are microchannels and/or the junction is a nanojunction. In yet another aspect, the junction can comprise an ion-selective membrane, for example, a Nafion membrane.

In an additional embodiment, the invention is directed to an electrochemical system comprising a substrate, a plurality of fluidic channels fabricated on said substrate, wherein at least two separate fluidic channels are connected by a junction, wherein at least one part of said substrate contains more than one set of microarrays. In some embodiments, the microchannels are separated by a pillar-free gap, for example having dimensions of about 25 to about 500 μm. The invention also encompasses the electrochemical system wherein a nanojunction connects said gap to a fluidic channel. In some embodiments when the electrochemical system comprises a pillar array, the average diameter of pillar is between about 0.1-1000 μm, or between about 1-100 μm, or between about 5-50 μm, between about 5-25 μm or between about 7-15 μm. In another aspect, the electrochemical system comprises a pillar array wherein the average pillar height is between about 1-1000 μm, or between about 1-500 μm, or between about 1-250 μm, or between about 5-100 μm, or between about 5-50 μm, or between about 5-25 μm. In certain embodiments, when the electrochemical system comprises a micropore array, the average diameter of pillar is between about 0.1-500 μm or between about 1-50 μm, or between about 2-25 μm and/or wherein the pore depth is between about 1-250 μm, or between about 2-200 μm, or between about 5-100 μm. In some embodiments, the substrate is made from polydimethylsiloxane.

In certain aspects, the invention is directed to electrochemical systems comprising a structure selected from a pillar array or micropore array in proximity to an electrode or an ion-selective membrane such that convection is spatially limited and/or the zone of ion depletion is reduced in size. In additional aspects, the invention is directed to a method of decreasing limiting current behavior or limiting convection near an electrode in an electrochemical system or enhancing electrode performance in an electrochemical system comprising providing an array of micropores or a pillar array in proximity to the electrode or to the ion-selective membrane such that convection is spatially limited and/or the zone of ion depletion is reduced.

The invention encompasses a method of decreasing limiting current behavior or limiting convection near an electrode in an electrochemical system or enhancing electrode performance in an electrochemical system comprising providing an array of micropores or a pillar array in proximity to the electrode such that convection is spatially limited and/or the zone of ion depletion is reduced. In certain additional embodiments, the electrochemical system comprises a support and an electrode. In certain embodiments, the micropore array or pillar array is positioned over the electrode. In some embodiments, the method comprises an array of micropores located over the electrode. The micropore array can, for example, be fabricated from a photoresist polymer, such as SU8. In some embodiments, the pore diameter is between about 10 and about 100 μm, or between about 10 and about 40 μm. In certain embodiments, the average distance between the pores of said array of micropores is between about 2 and about 100 μm or between about 20 and about 50 μm. In certain aspects, the depth of each of the pores of said array is between about 10 and 100 um. In some embodiments, the method comprises an electrochemical system comprising a microchannel wherein the microchannel is fabricated from PDMS.

In yet an additional aspect, the invention includes an electrochemical system comprising a micropore electrode seated in a reservoir, an electrolyte, a substrate and a support, wherein said substrate comprises one or more microchannels and wherein said micropore electrode comprises an electrode and a micropore array, wherein said micropore array is placed over said electrode. In some embodiments, the micropore array is fabricated from a photoresist polymer, such as SU8. In some embodiments, the pore diameter is between about 10 and about 100 μm, or between about 10 and about 40 μm. In certain embodiments, the average distance between the pores of said array of micropores is between about 2 and about 100 μm or between about 20 and about 50 μm. In certain aspects, the depth of each of the pores of said array is between about 10 and about 100 um. In a further embodiment, the invention is an electrochemical system comprising an electrode seated in a reservoir, a pillar array placed over said electrode, an electrolyte, a substrate and a support, wherein said substrate comprises one or more microchannels. In certain aspects, the average diameter of a pillar is between about 0.1-1000 μm, or between about 1-100 μm, or between about 5-50 μm, between about 5-25 μm or between about 7-15 μm. In another the electrochemical system comprises a pillar array wherein the average pillar height is between about 1-1000 μm, or between about 1-500 μm, or between about 1-250 μm, or between about 5-100 μm, or between about 5-50 μm, or between about 5-25 μm. Also included in the present invention are methods of limiting convection near an electrode in an electrochemical system or enhancing electrode performance in an electrochemical system comprising providing an electrochemical system described herein.

The invention also encompasses a method of limiting convection near an electrode in an electrochemical system or enhancing electrode performance comprising providing non-planar structures suspended over the electrode, wherein said suspended non-planar structures are not in direct contact with the electrode therefore maintaining the active surface area of the electrode. In certain aspects, the non-planar structures are an array of micropores. In certain additional aspects, the non-planar structures are an array of pillars.

The invention also includes methods of increasing the electrochemical efficiency of an electrode or an ion-selective membrane comprising decreasing the spatial extent of the ion depleted region. The spatial extent of the ion depleted region can be reduced by incorporating in the electrochemical system a structure described herein (for example, a pillar array or a micropore array). As described in more detail below, the smaller the ion depletion region, the greater the electrochemical efficiency of the system.

Also encompassed in the present invention are fuel cells and/or biosensors comprising an electrochemical system described herein.

BRIEF DESCRIPTION OF THE DRAWINGS

FIGS. 8A and 8B: Exploded schematic view of micro-pore electrode and snapshots of planar (bare) (B) and micro-pore electrodes (A).

DETAILED DESCRIPTION OF THE INVENTION

As used herein, "a" or "an" are taken together to mean one or more unless otherwise specified.

In part, the invention relates to a method of reducing or eliminating limiting-current behavior in the operation of electrochemical systems, in particular those with ion-selective membrane or electrochemical electrodes, by spatially reducing the convection near the membrane or electrode. An electrochemical reaction is one that takes place at an interface between the electrodes and the electrolyte. The invention relates to electrochemical systems in which non-planar structures such as micropore arrays, microarrays or pillar arrays are used to reduce convection in comparison to conventional systems without such structures. The reduction in convection results in a reduction in the size or extent of the zone of ion depletion. The terms "zone of ion depletion", "ion-depleted region," "zone of depletion," and "depletion zone" are used interchangeably herein. The zone of ion depletion is the area in proximity to the electrode surface or the membrane where the concentration of ions is depleted or the region of interest where the electro-active ions have been consumed. In the case of the pillar array located on the anodic side of a nanojunction connecting parallel microchannels such as described in the examples section, the zone of depletion can, for example, be confined to the distance set by the distance between the nanojunction and the pillars. In the case of a micropore array set over an electrode as described in the examples below, the zone of depletion can be confined within the micropore structure.

Figure 1A:
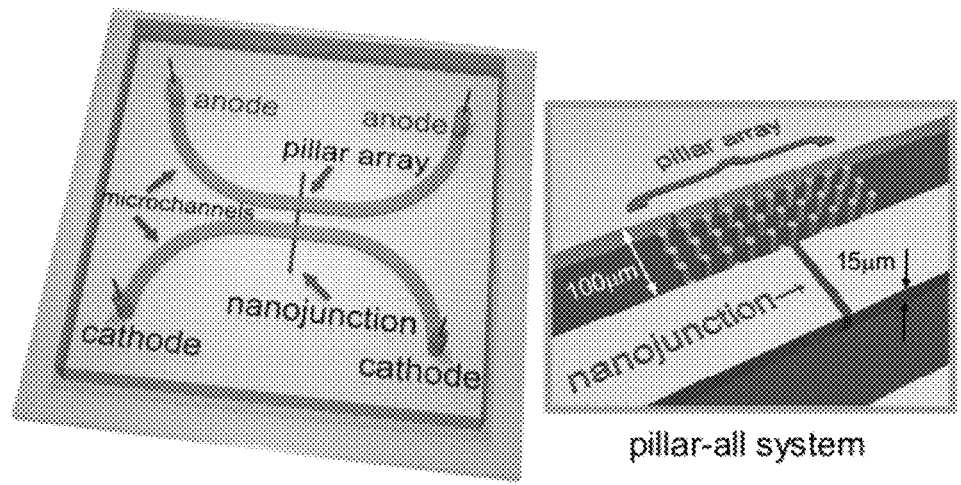
FIG. 1A: Schematic diagram of microchannel/nanojunction hybrid system with pillars. PDMS substrate having microchannels and vertical nanoporous junctions bonded with a glass support.

While the local convection could be promoting over-limiting current, strong circulatory vortices may be defining the extent of ion-depleted region. Without being bound by any particular theory, it is postulated that limiting the size of circulatory flow would lead to a smaller ion depletion region, and the effective reduction or elimination of limiting current behavior. As such, the invention is generally applicable to engineering strategies for electrodes and fuel cells in order to reduce current limitation posed by concentration overpotentials and concentration changes near such electrochemical systems. This concept can be demonstrated by performing experiments in microfluidic systems. In the microfluidic channel, one can control the degree of convection allowed by fabricating designed structures such as pillar arrays or micropore arrays in order to localize the convective flow in the middle of microchannels, such as shown in FIG. 1A. Since the strong convective flow is generated inside the ion depletion zone, the pillars can be patterned at the anodic side of microchannel.

Ion-selective or ion-exchange membrane refers to membranes that allow the passage of the ions, while substantially maintaining the integrity between the contents separated by the membrane. The particular material selected for membrane can be changed for the electrode materials selected and the desired rate of exchange of ions. Examples of ion-selective membranes include high aspect ratio ion-selective membranes made from polytetrafluroethylenes, perfluorosulfonates, polyphosphazenes, polybenzimidazoles, poly-zirconia, polyethyleneimine-poly(acrylic acid), poly(ethylene oxide)-poly(acrylic acid) and non-fluorinated hydrocarbon polymers. A preferred membrane is selected from Nafion, CMI 7000, Membranes International C/R, CMB and CCG-F from Ameridia, AM-1, AM-3 and AM-X and PC-200D.

In one embodiment, a device may contain a plurality of high aspect ratio, ion selective membranes. In one embodiment a plurality of high-aspect ratio ion selective membranes can be fabricated on a chip. In one embodiment fabrication of a plurality of high-aspect ratio ion selective membranes may be done using multi-blade fabrication. In one embodiment multi-blade fabrication can be used for commercialization of a device containing a self-sealed membrane. In one embodiment a self-sealed membrane refers to the high aspect ratio ion selective membrane. In one embodiment "self-sealed" means that after infiltration, or passage or filling of the trench or the gap, or the scratch made by the blade with a liquid polymer solution, unbending the chip and solidifying the polymer causes a self-sealing process of the scratch or the gap or the trench by the polymer.

In one embodiment, multi-blade fabrication can be used for massive parallelization of the membrane or the device fabrication process. In one embodiment, multi-blade fabrication can be used to make a plurality of membranes in parallel. In one embodiment, multi-blade fabrication renders the fabrication process fast. In one embodiment, multi-blade fabrication renders the device a low-cost device. In one embodiment multi-blade fabrication is combined with multi-syringe or multi-dispenser system that enables parallel injection of liquid polymer to all trenches or cuts made by the multiple blades. In one embodiment, the multi-blade fabrication technique is part of an automated fabrication technique, in which all steps of forming the high aspect ratio ion selective membranes are automated, and all steps are performed in parallel on many channels or on many device parts or on many devices. In one embodiment, such automation enables mass production of devices, low cost, high yield and reproducibility of device properties. In one embodiment parallel multi-blade fabrication facilitates quality control and reliability measurements to be done on selected devices. In one embodiment, multi-blade fabrication and/or automation of the process is achieved using computers, computer programs, robotics or a combination thereof. In one embodiment, the number of high aspect ratio ion selective membranes produced is equal to the number of channels described herein above. In one embodiment the number of high aspect ratio ion selective membranes produced is greater than the number of channels described herein above. In one embodiment, the number of high aspect ratio ion selective membranes produced is smaller than the number of channels described herein above. In one embodiment, the number of high aspect ratio ion selective membranes produced is more than 5, or, in other embodiments, more than 10, 96, 100, 384, 1,000, 1,536, 10,000, 100,000 or 1,000,000 channels, or in any number desired to suit a particular purpose.

A pillar array has a plurality of pillars. In some embodiments, the pillar diameter is between about 0.1-1000 μm, preferably between about 1-100 μm, more preferably between about 5-50 μm, more preferably between about 5-25 μm, more preferably between about 7-15 μm. In some embodiments, the average pillar size was between about 1-1000 μm. In some embodiments, the average pillar size was between about 1-500 μm. In some embodiments, the average pillar size was between about 1-250 μm. In some embodiments, the average pillar size was between about 5-100 μm. In some embodiments, the average pillar size was between about 5-50 μm. In some embodiments, the average pillar size was between about 5-25 μm. In some embodiments the average distance between the pillars in the pillar array are between about 0.1-500 μm. In some embodiments the average distance between the pillars in the pillar array are between about 1-100 μm. In some embodiments the average distance between the pillars in the pillar array are between about 5-50 μm. In some embodiments the average distance between the pillars in the pillar array are between about 5-25 μm.

A micropore array has a plurality of micropores. In some embodiments, the pore diameter is between about 0.1-500 μm. In certain embodiments, the pore diameter is between about 10-100 μm. In some embodiments, the pore diameter is between about 1-50 μm. In additional aspects, the pore diameter is between about 10-40 μm. In some embodiments, the pore diameter is between about 2-25 μm. In some embodiments, the pore diameter is between about 5-20 μm. In some embodiments, the pore depth is between about 0.1-500 μm. In some embodiments, the pore depth is between about 1-250 μm. In some embodiments, the pore depth is between about 2-200 μm. In some embodiments, the pore depth is between about 5-100 µm. In additional aspects, the pore depth is between about 10-100 µm. In some embodiments the average distance between the pores in the micropore array are between about 1-500 µm. In some embodiments, the distance between the pores in the micropore array are between about 2-250 µm. In some embodiments, the distance between the pores in the micropore array are between about 2-100 µm. In some embodiments, the distance between the pores in the micropore array are between about 5-75 µm. In some embodiments, the distance between the pores in the micropore array are between about 10-50 µm. In additional embodiments, the distance between the pores is between about 20-50 µm.

In some embodiments, more than one set of micropores/pillar arrays are present, where the gap between the sets of arrays is at least about 50% greater than the average distance between the individual pillars/pores in the array. In some embodiments, the gap between the arrays is between about 10-1000 µm. In some embodiments, the gap between the arrays is between about 25-500 µm. In some embodiments, the gap between the arrays is between about 25-200 µm.

In one embodiment, the width of the microchannel is between about 0.1-500 µm, and in one embodiment, the width of the channel is between about 5-200 µm. In some embodiments, the width of the channel is between about 20-1200 µm. In some embodiments the width of the channel is between about 50 and 500 µm. In some embodiments the width of the channel is between about 50 and 250 µm.

In some embodiments, the depth of the microchannel is between about 0.5-200 µm, and in some embodiments, the depth of the channel is between about 5-150 µm. In some embodiments, the depth of the channel is between about 5-100 µm. In some embodiments, the depth of the channel is between about 5-50 µm. In some embodiments, the depth of the channel is between about 5-25 µm. In some embodiments, the depth of the channel is between about 10-25 µm. In some embodiments, the depth of the channel is between about 10-20 µm.

In some embodiments, the ion-selective membrane has a width of between about 0.01-100 µm, and in some embodiments, the width of the ion-selective membrane is between about 1-10 µm. In some embodiments, the ion-selective membrane has a width of between about 100-500 nm. In some embodiments, the ion-selective membrane has a depth of between about 0.01-3000 µm, and in some embodiments, the depth of the ion-selective membrane is between about 10-500 µm and in some embodiments, the depth of the ion-selective membrane is between about 100-1000 µm. In some embodiments, the ion-selective membrane has a depth of between about 500-1100 µm. In some embodiments, the membrane is cation selective. In some embodiments, the membrane is anion selective.

In some embodiments, the fluidic chip comprises a silicon polymer, preferably, polydimethylsiloxane (PDMS). In some embodiments, the fluidic chip has a hydrophobic surface. In some embodiments, the fluidic chip comprises an elastomeric polymer. The elastomeric polymer can be a silicone elastomeric polymer. The elastomeric polymer can be solidified by curing. In some embodiments, the elastomeric polymer can be treated with high intensity oxygen or air plasma to permit bonding to the compatible polymeric or non-polymeric media. The polymeric and non-polymeric media can be glass, silicon, silicon oxide, quartz, silicon nitride, polyethylene, polystyrene, glassy carbon, or epoxy polymers.

Construction of the microchannels may be accomplished according to, or based upon any method known in the art, for example, as described in Z. N. Yu, P. Deshpande, W. Wu, J. Wang and S. Y. Chou, *Appl. Phys. Lett.*, 77 (7), 927 (2000); S. Y. Chou, P. R. Krauss, and P. J. Renstrom, *Appl. Phys. Lett.*, 67 (21), 3114 (1995); Stephen Y. Chou, Peter R. Krauss and Preston J. Renstrom, *Science*, 272, 85 (1996), U.S. Patent Publication 20090242406, and U.S. Pat. No. 5,772,905, which are incorporated herein by reference. In one embodiment, the microchannels can be formed by imprint lithography, interference lithography, self-assembled copolymer pattern transfer, spin coating, electron beam lithography, focused ion beam milling, photolithography, reactive ion-etching, wet-etching, plasma-enhanced chemical vapor deposition, electron beam evaporation, sputter deposition, stamping, molding scanning probe techniques and combinations thereof. In some embodiments, the methods for preparation of the devices of this invention may comprise or be modifications of Astorga-Wells J., et al, *Analytical Chemistry*, 75: 5207-5212 (2003); or Joensson, M. et al, Proceedings of the MicroTAS 2006 Symposium, Tokyo Japan, Vol. 1, pp. 606-608. Alternatively, other conventional methods can be used to form the microchannels. In one embodiment, the microchannels are formed as described in J. Han, H. G. Craighead, *J. Vac. Sci. Technol., A* 17, 2142-2147 (1999) and J. Han, H. G. Craighead, *Science*, 288, 1026-1029 (2000), hereby incorporated fully herein by reference.

In one embodiment, a series of reactive ion etchings are conducted, after which nano- or micro-channels are patterned with standard lithography tools. In one embodiment, the etchings are conducted with a particular geometry, which, in another embodiment, determines the interface between the microchannels, and/or nanochannels. In one embodiment, etchings, which create the microchannels, are performed parallel to the plane in which etchings for the nanochannels are created. In another embodiment, additional etching, such as, for example, and in one embodiment, KOH etching is used, to produce additional structures in the device, such as, for example, for creating loading holes.

In one embodiment, an interface region is constructed which connects the channels on the chip, for example two microchannels. In one embodiment, diffraction gradient lithography (DGL) is used to form a gradient interface between the channels of this invention, where desired. In one embodiment, the gradient interface region may regulate flow through the concentrator, or in another embodiment, regulate the space charge layer formed in the microchannel, which, in another embodiment, may be reflected in the strength of electric field, or in another embodiment, the voltage needed to generate the space charge layer in the microchannel. In some embodiments, the ion-selective membrane is positioned at such an interface.

In another embodiment, the device may contain at least two pairs of electrodes, each providing an electric field in different directions. In one embodiment, field contacts can be used to independently modulate the direction and amplitudes of the electric fields to, in one embodiment, orient the space charge layer, or a combination thereof.

In some examples, the electrochemical systems and methods described herein can be used in devices and applications which are associated with electrode polarization, such as concentration polarization. Non-limiting examples of such devices and applications include solid oxide fuel cells (SOFCs), lithium ion batteries, biosensors and dielectric spectroscopy-based sensors.

By limiting the lateral dimension of the local circulating flow near a membrane or electrode, a reduction in the limiting current behavior can be achieved resulting in enhanced ion transport. In some embodiments, the current behavior can be limited by addition of the structural feature described herein without modifying the chemistry or physics of the electrode or membrane operation.

EXAMPLES

Example 1

Electrochemical System Composed of Two Parallel Microchannels Connected by Nanochannels (or a Nanoporous Membrane)

Compared to the classical membrane geometry that blocked a straight channel, fluid flow in one embodiment is not blocked by the membrane but rather flows along it. The polydimethylsiloxane (PDMS) microfluidic chips were fabricated with perm-selective nanojunctions using the previously published methods. (S. J. Kim, and J. Han, *Anal. Chem.* 80, 3507 (2008)). The anodic and cathodic microchannel had the dimension of about 100 µm width×15 µm depth. Pillar arrays were fabricated at the anodic side of microchannel and they had the size of about 10 µm diameter (about 15 µm height). The gap between each pillar was about 10 µm. Separated pillar systems had either about 100 µm or about 50 µm distance between two groups of pillar arrays. A Nafion (sulfonated tetrafluoroethylene based fluoropolymer-copolymer) nanojunction was infiltrated at the center of pillar structures.

1 mM of potassium phosphate dibasic solution (pH=8.4) was used as main buffer solution and it contained 1 µg/ml of FITC for fluorescent tracking. All the flow patterns were imaged with an inverted fluorescence microscope (Olympus, IX-51) and a CCD camera (SensiCam, Cooke corp.). Sequences of images were analyzed by Image Pro Plus 5.0 (Media Cybernetics Inc.). A DC power supply (Keithley 236 source measure unit (SMU)) was used to apply electrical potential to each reservoir through a voltage divider. As shown in FIG. 1A, Ag/AgCl electrodes (A-M Systems, Inc.) were placed into each reservoir for proper electrical connections. At the same time, the ionic current through nanojunctions was also measured by Keithley 236 SMU. The sequence of current was analyzed by commercial software, LabView 8.2 (National Instrument). For the ionic current with constant applied voltages, the same voltages were applied at the anodic sides, while the cathodic sides were electrically grounded. The currents were measured at every 0.1 second. For measuring Ohmic/limiting/over-limiting current, voltages at the anodic sides were ramped up from 0V to 80V at the rate of 0.2V/30 sec.

Figure 1B:
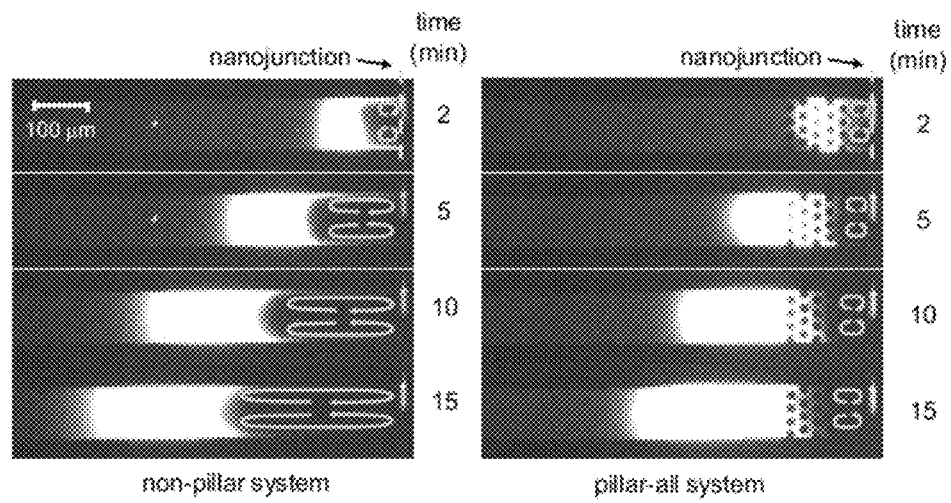
FIG. 1B: Sequences of fluorescent images of depletion boundary near nanojunctions for nonpillar and pillar array (pillar-all) system. 30V (left)-15V (right) was applied at the anodic side microchannel.
Figure 2A:
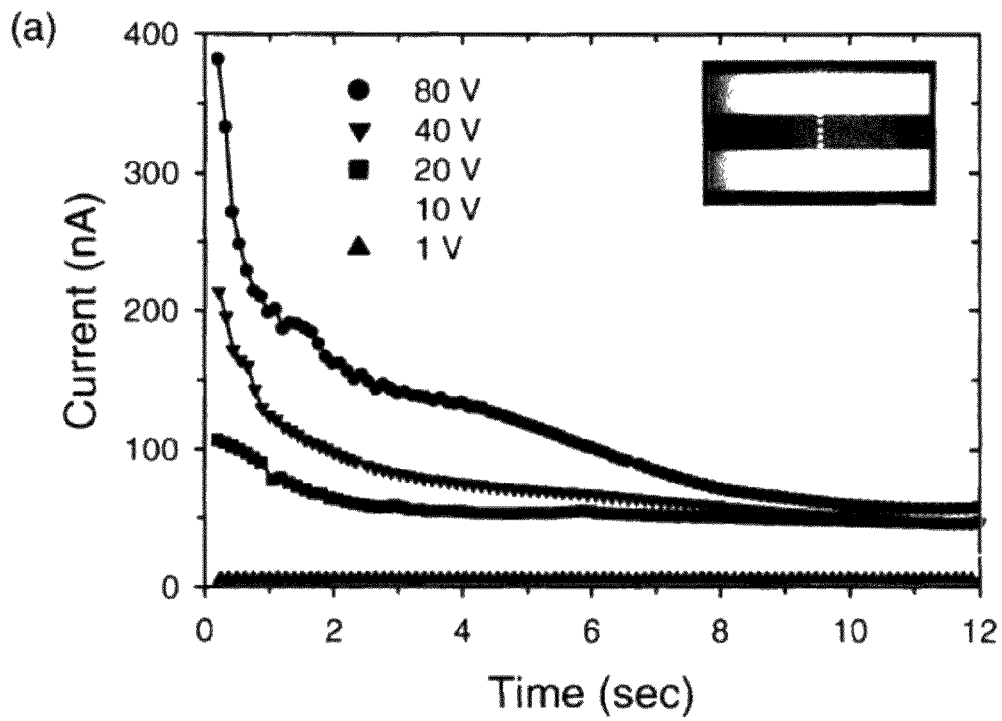
FIG. 2A: Plots for current drop through nanojunction as a function of time (fixed voltage) in non-pillar system.
Figure 2B:
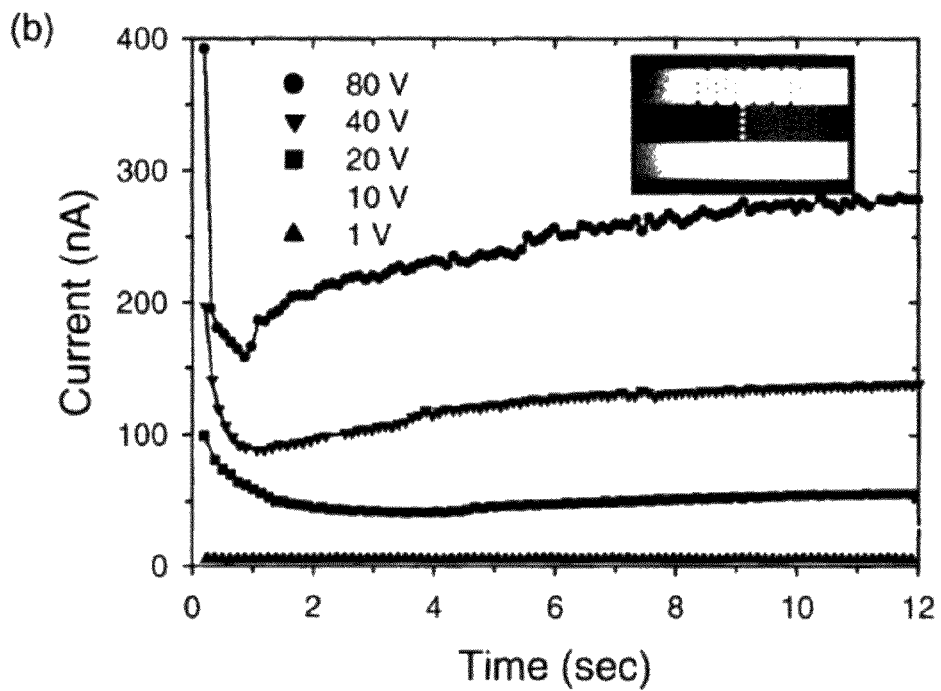
FIG. 2B: Plots for current drop through nanojunction as a function of time (fixed voltage) in pillar array system showing significant difference in current level.
Figure 3A:
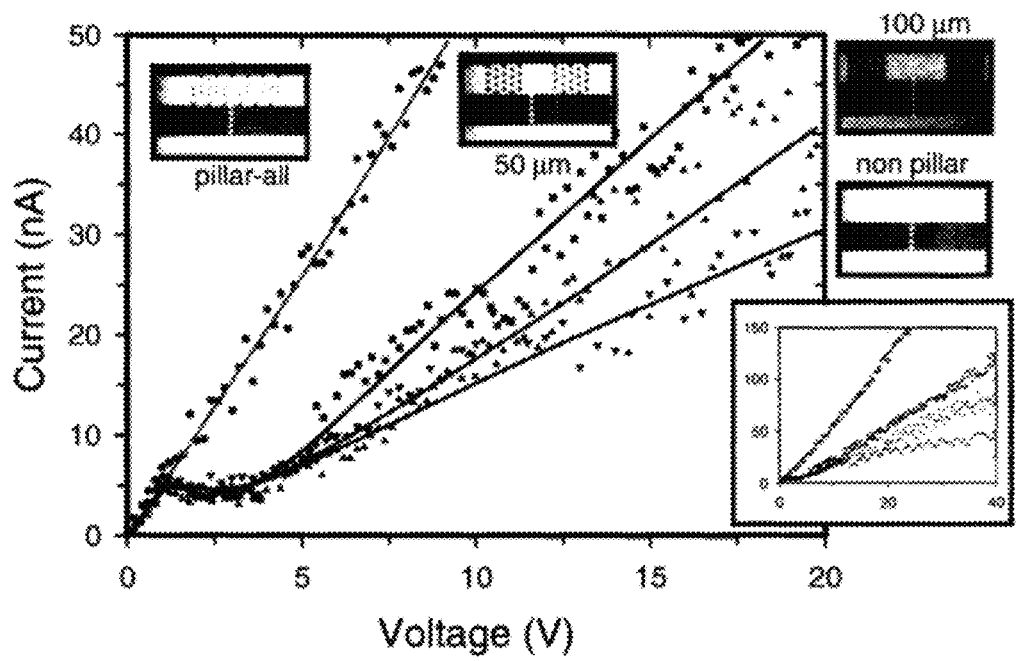
FIG. 3A: I-V plot for with/without pillars showing Ohmic/limiting/over-limiting current. 1 mM phosphate buffer solution was used. Also the current behavior in the separated pillar system (50 μm and 100 μm) was shown.

From fluorescent images in FIG. 1B, the fluid vortex generated in the pillar-array system was shown to be mostly confined between pillars, while the vortex (related to the size of depletion zone) continuously expanded their size in non-pillar system. In the pillar-array system where laterally limited vortex was observed, the following effects were observed; 1) the concentration gradient was maintained at higher level so that diffusive transport of ion is promoted, while it quickly reaches near zero with rapidly expanding depletion region in a nonpillar system; and 2) shorter diffusion length (lower overall electrical resistance) results in higher electric field, which is the driving force of drift ion transport, inside the depletion zone. These attributions were confirmed by measuring ionic currents through the nanojunctions as functions of both time and applied voltage as shown in FIGS. 2A, 2B and FIG. 3A. In the first case (FIG. 2A), the constant voltages were suddenly applied at both anodic side microchannels, while the cathodic microchannels were electrically grounded. At low voltages (e.g., 1 V in FIGS. 2A and 2B), time-independent currents were observed in both systems because the ion current did not reach the limiting current regime yet at such low voltages. While the non-pillar channel shows precipitous drop in ionic current due to the formation of ion depletion zone (i.e., continuously increasing electrical resistance) at higher applied voltages as shown in FIG. 2A, ion currents in the pillar-all system recover from the initial drop and increased up to ~70% of the original level as shown in FIG. 2B, demonstrating an effective elimination of current suppression caused by depletion. The initial current drop in pillar-array system was due to the formation of ion depletion zone within the interpillar distance.

Example 2

Limiting/Over-Limiting Current Behavior

Figure 3B:
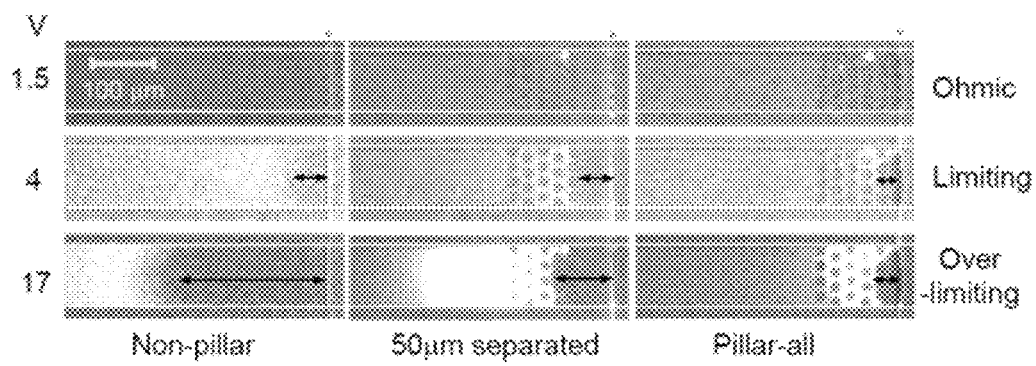
FIG. 3B: Sequence of fluorescent images of growing depletion zone for non-pillar, 50 μm separated pillar and pillar array system.

The current-voltage characteristics across the nanojunction were measured to characterize their detailed limiting current behaviors. In addition to the pillar and non-pillar systems shown in FIG. 1B, two additional systems were fabricated with a defined gap between pillar array and the nanojunction (50 µm and 100 µm) as shown in the microscopic insets of FIG. 3A. The I-V traces for all systems largely overlapped in the sub-limiting current regime (less than 2V). The fluorescent images less than 2V did not have any changes in all systems as shown in FIG. 3B. However, critical differences were observed between pillar and non-pillar systems, in that (1) the limiting current behavior was almost eliminated in the pillar-array system, (2) overall current level was higher in any kind of pillar system than in the non-pillar system. Confined vortex leads to much shorter diffusion lengths in any pillar systems along over-limiting current regimes as confirmed by the fluorescent images (FIG. 3B), leading to higher diffusive and drift ion-flux. These effects were seen more clearly in the two separated-pillar systems. Due to the space between the pillar arrays, the depletion zone initially formed just as in non-pillar systems. At this moment, the limiting current behavior was observed as usual. This can also be seen by the fact that the I-V traces for distanced-pillar and non-pillar systems are overlapping in the limiting current regime (at 5 nA in the voltage range of 2V-4.5V). As the voltage increased above the limiting regime, however, the lateral size of the fluid vortex are essentially determined by the distance between the pillar array and the nanojunction, since the depletion boundary is 'pinned' at the pillar array and cannot expand any more as shown in FIG. 3B. In such conditions, the resulting (over-limiting) current levels were much higher than that of non-pillar system. For example, the lengths of depletion boundary were approximately 250 µm (non-pillar system) and 60 µm (pillar-all system) at 17V (FIG. 3B) and their current values were 25 nA (non-pillar system) and 100 nA (pillar-array system) (FIG. 3A). Importantly, the current level of each system was highly correlated with the distance between pillar structures as observed in two separated pillar systems. Since the amplified electrokinetic vortical flows were dominant inside the depletion zone, shorter gap (50 µm) enforced relatively higher electric field and higher concentration gradient than wider gap (100 µm). As a result of this, the over-limiting current of 50 µm-separated pillar system had increased faster than 100 µm separated system. The inset plot in FIG. 3A shows the distinct difference of over-limiting current behaviors between each system (wider x- and y-axis range).

From the experimental results of FIG. 3A, one can conclude that the extent of over-limiting current behavior is related to the lateral size of the depletion zone, which in turn is determined by the convection profile. In a pillar system, depletion region does not expand much more than the distance from the nanojunction to the nearest pillar, leading to a near-complete elimination of limiting current behavior. In the non-pillar and 50 μm/100 μm separated pillar systems, depletion region can start to expand when the bias reaches the critical point (2V, near the onset of the limiting current). In the 50 μm and 100 μm separated pillar systems, depletion region was ultimately confined to the distance set by the distance between the nanojunction and the pillars. The shorter this distance is, the lower overall resistance in the overlimiting current regime. This is reflected in the different slopes in FIG. 3A. However, doubled distance did not exactly impose doubled resistance (slope of 1-V curve) because the concentration distribution inside the depletion zone could be altered by addition parameters such as the degree of convection and an EOF through the microchannel, etc.

Example 3

Confining Convection Using Narrow Microchannel

Figure 5A:
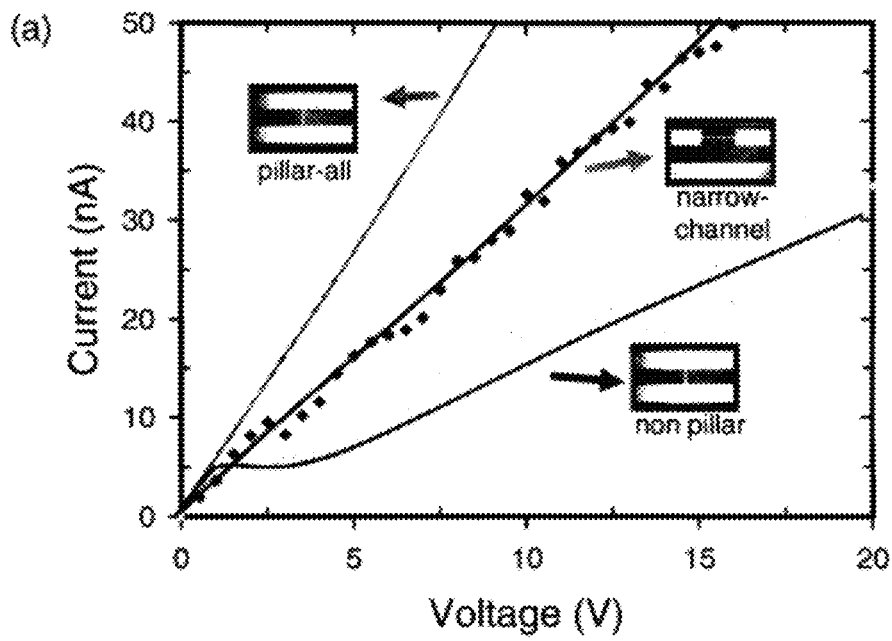
FIG. 5A: Pillar array, narrow-channel and non-pillar systems showing the unstable current behavior in a non-pillar system. I-V curve of narrowed channel had moderate slope compared to pillar and non-pillar system.
Figure 5B:
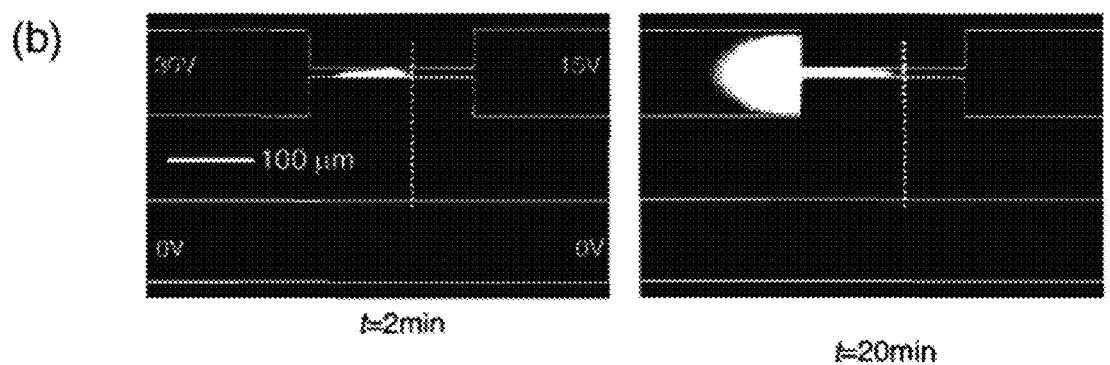
FIG. 5B: Snapshots of fluorescent images of depletion zone growth.

In another scenario, we narrowed down the microchannel width of the non-pillar system only around the nanojunction as shown in inset of FIG. 5A. The narrow region has only 10 μm width (200 μm length). Due to high flow resistance, the current through the groove decreased such that a direct comparison to pillar system could not be made. Thus, in the Ohmic current region <2V), I-V curve of narrowed channel had moderate slope compared to pillar and non-pillar system as shown in FIG. 5A. However, the groove was able to limit the convection and hold the depletion zone into the narrowed region as shown in FIG. 5B. The density of electric field inside the narrowed region is geometrically 10 times larger than outside the region. Furthermore, the electric field inside the depletion zone can be amplified more than 30 times greater than one outside the depletion zone. These combined effects gave an extremely high gradient of electric field at the narrowed region interfaces and would play a significant role of holding the depletion zone inside the narrowed region. With aforementioned consideration, the limiting current behavior almost disappeared and the current level was much higher than non-pillar system as shown in FIG. 5A.

Example 4

Enhancing the Stability of Electrochemical Membrane Systems

Figure 4:
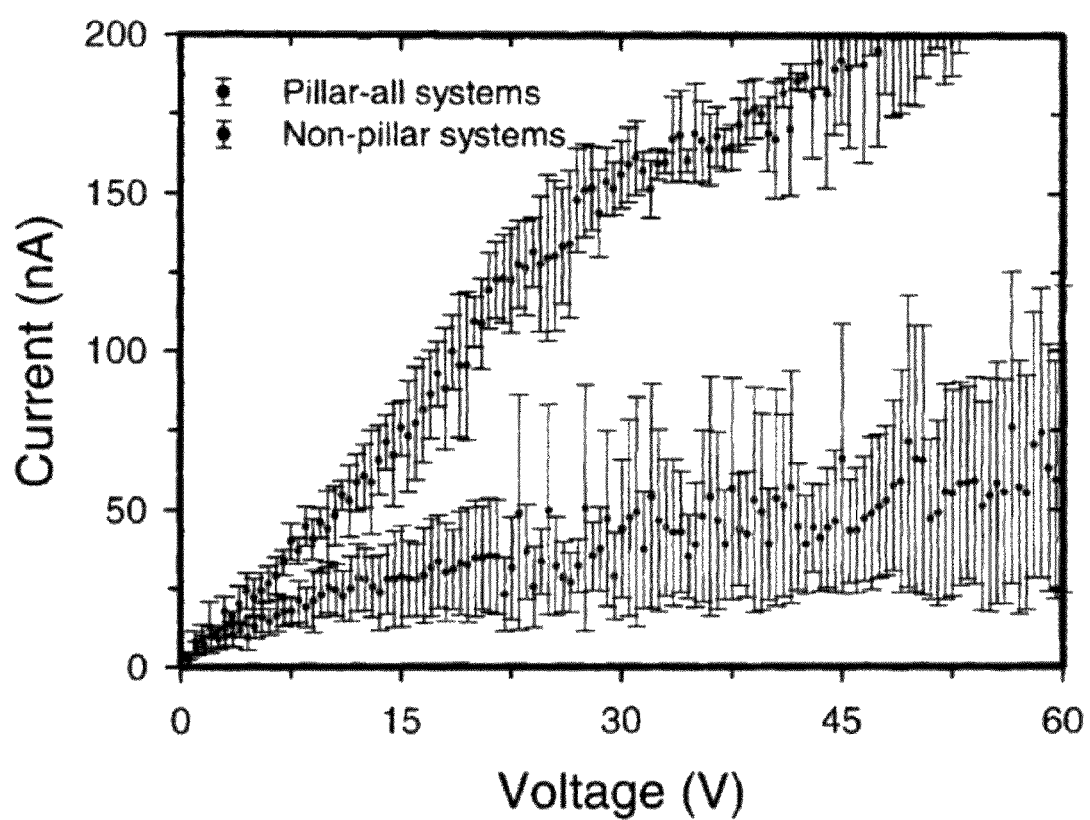
FIG. 4: I-V plot for pillar all and non-pillar systems.

The pinned depletion boundary also significantly affects the stabilities of measured current behavior (current fluctuation) which is the deterministic factor for the performance of the ICP related applications. As shown in FIG. 4, the current plot of non-pillar system had large standard deviation, while most of the values were overlapped in the case of pillar-all system. In a non-pillar system the depletion region is constantly expanding, changing the system resistance, concentration profile and (electroosmotic) flow dynamically. While this could be the source of the instability and run-to-run variability, the confinement of convection (and depletion zone) in pillar systems eliminates dynamical changes in resistance/current. Therefore, the defined depletion zone would induce more stable performance of the membrane system.

Example 5

Limiting Convection Near Electrodes by Microstructures

Single Electrode Systems

Enhancing the performance of an electrochemical system can be achieved by optimizing various factors such as electrode/membrane characteristics, used electrolyte and catalysts. For example, during microfluidic fuel cell operation, a concentration boundary layer (ICP layer) that depends on channel geometry and flow rate will develop in the channel, starting at the leading edge of the electrode. Thus, the maximum current density of the fuel cell is determined by the rate of the convective/diffusive mass transport from the bulk to the surface of the electrode under the assumption of rapid electrochemical reaction. For limiting case, the oxidant/fuel concentration is zero at the entire surface of the electrode, meaning high electrical resistance which lowers the total performance of fuel cell. In order to enhancing diffusive transport, one can use line electrodes, to which the diffusive ion transport occurs in two directions (2D diffusion-drift), or use planar electrodes (1D diffusion-drift). In addition, point electrodes (3D diffusion-drift) can also be used. Planar type electrochemical membranes and electrodes generally increase the overall (membrane/electrode) surface area.

Figure 6A:
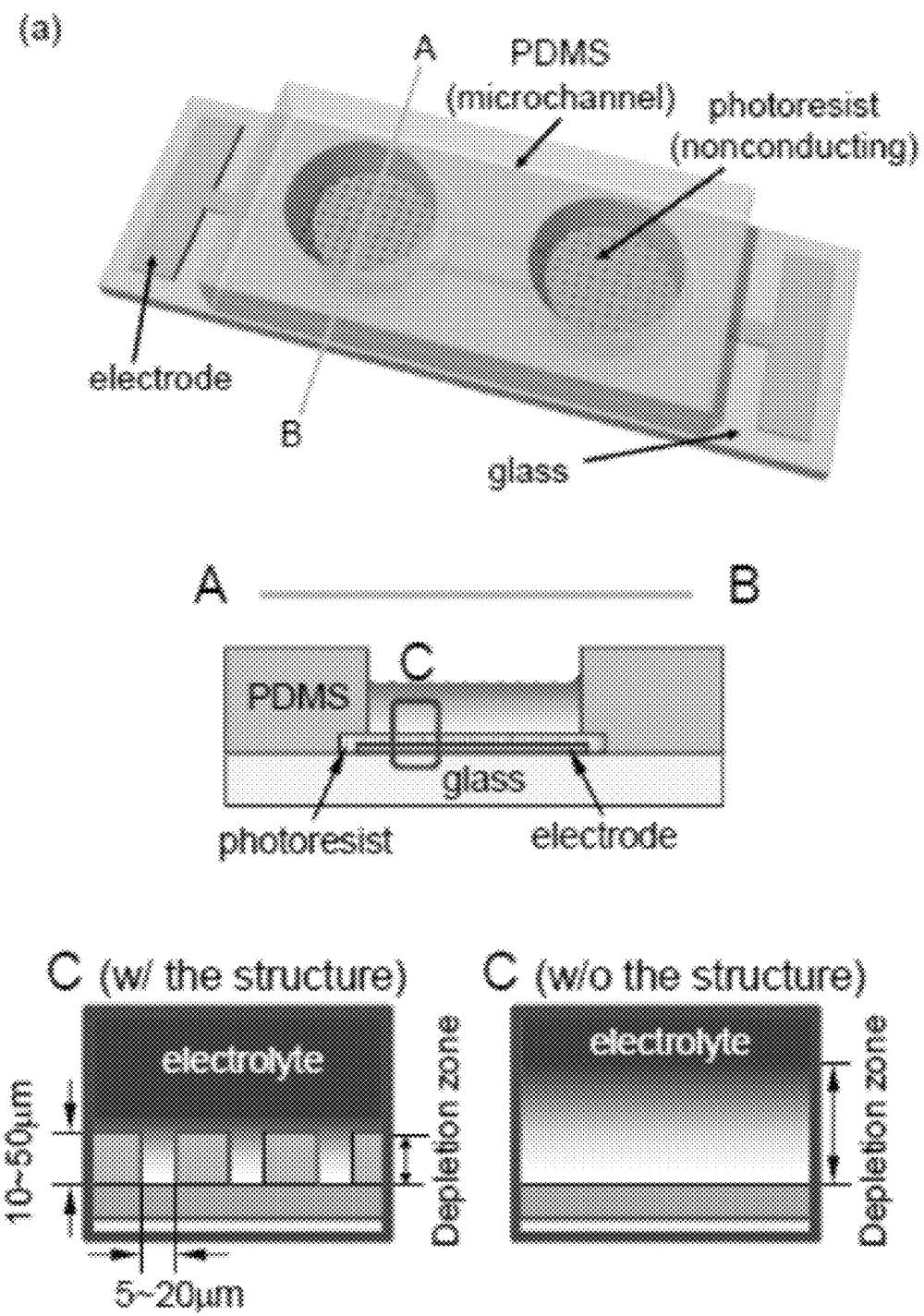
FIG. 6A: Schematic diagram of the micro-hole structure that can hold the depletion zone on top of the electrode.
Figure 6B:
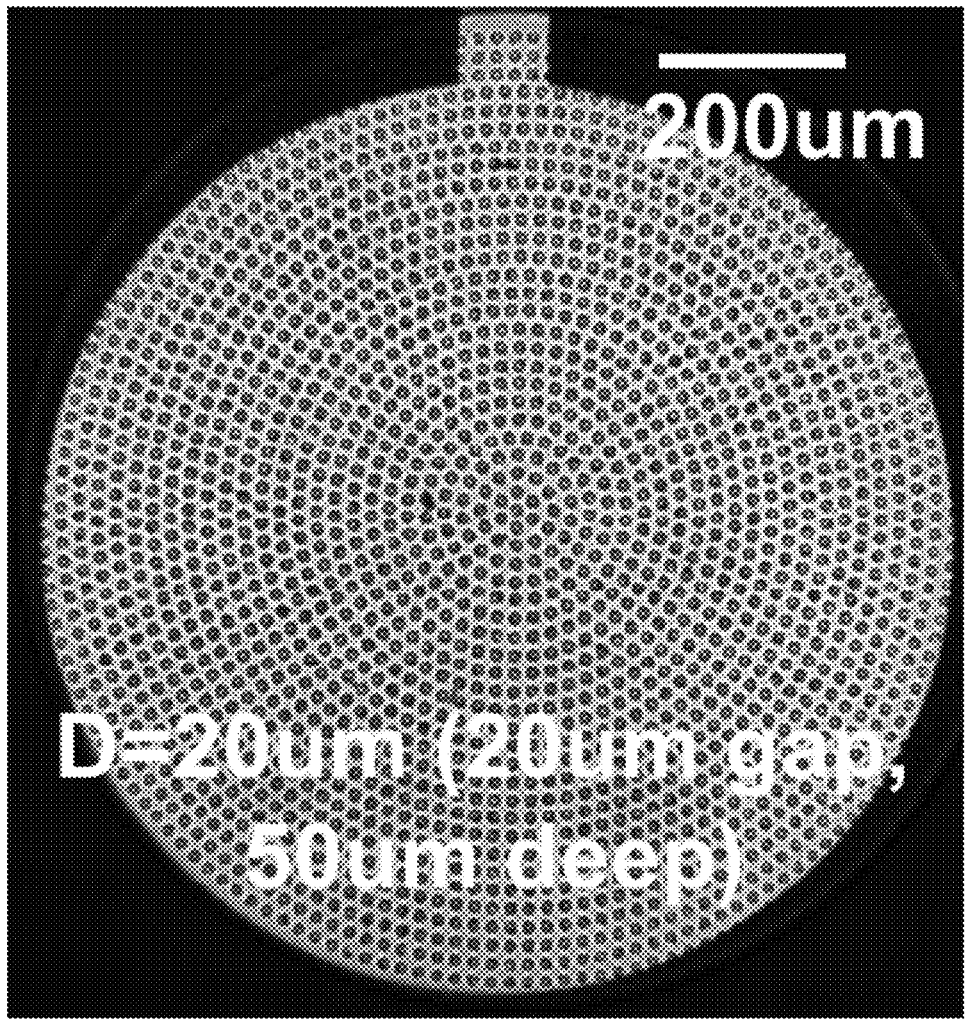
FIG. 6B: Fabricated micro-hole structure on top of the electrodes.
Figure 6C:
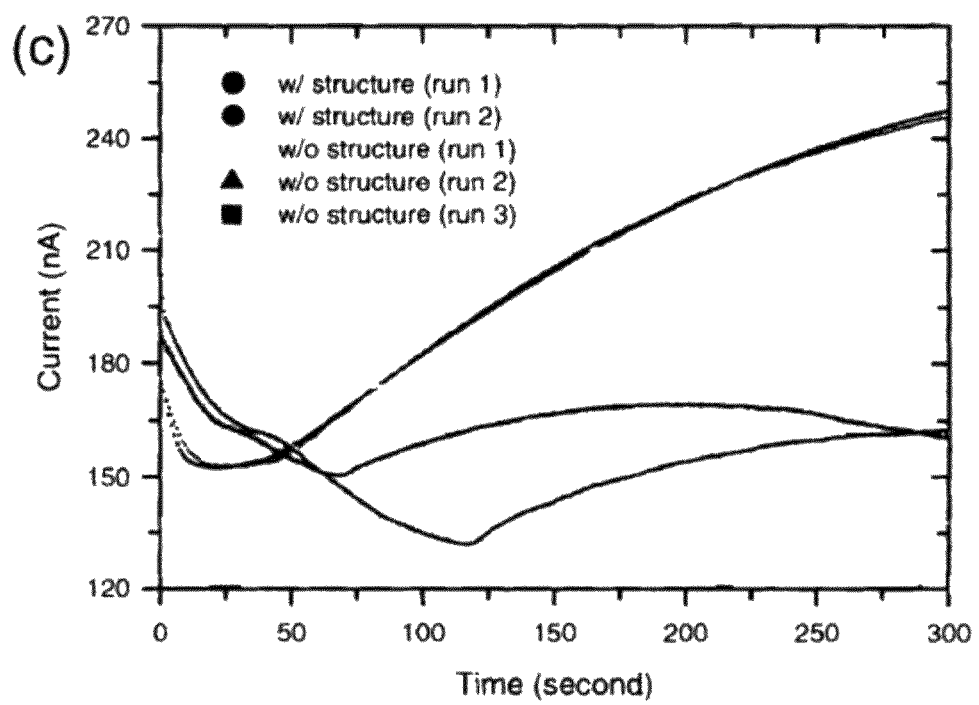
FIG. 6C: Comparison of the current behavior at 5V applying voltage with and without the micro-hole structure.
Figures 7A, 7B, 7C:
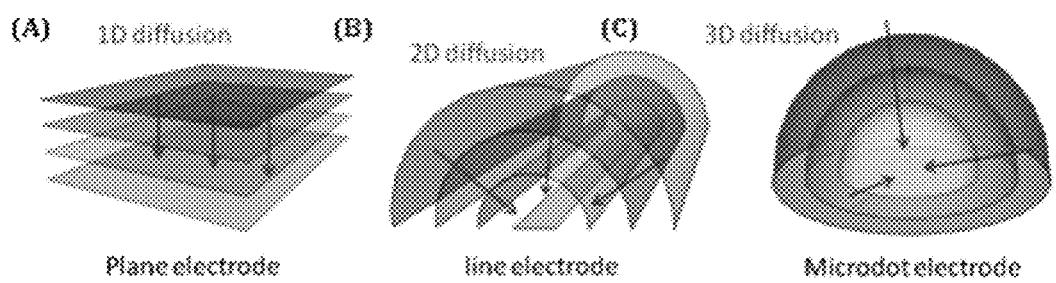
FIGS. 7A-7C: Difference between planar vs. microelectrode. (A) In the planar electrode, depletion zone is formed in a planar fashion, and the diffusion of charge carriers toward the electrode is inefficient. As a result, the concentration overpotential is significant. (B) and (C), in the line-patterned or dot-patterned microelectrodes, the diffusional pattern is either 2D or 3D, which is more efficient. Depletion zone is limited in length, which leads to smaller concentration overpotentials.

In one example, micro-pore structures on top of planar electrode with non-conducting materials were fabricated, as shown in FIG. 6A. Simple photoresist polymer such as SU8 (MicroChem Inc.) can be used for fabrication. This electrode system was similar to point electrodes system. As shown in FIG. 6A, the micro-pore structure, which has the dimension of about 5-100 μm depth and about 5-20 μm diameter, can hold the depletion zone thickness down to distance determined by the thickness (height) of the pore, by similar mechanism to the narrow microchannel case. FIG. 6B shows the fabrication of the micro-hole structure on top of the electrode. In some examples, the micro-holes are about 20 μm in diameter, about 20 μm in distance between each hole and about 50 μm in height. With this pattern on the electrodes, the current behaviors at 5V constantly applying voltage were measured by Keithley 6514 electrometer as shown in FIG. 6C. With the structure, the initial dropped current, which was caused by initial formation of depletion zone, recovered quickly, while the current dropped and fluctuated without the structure. This result showed that the current (power density) in the system would be greatly enhanced because the high electrical resistance due to the depletion zone could be confined within the micro-pore structure. This strategy can be applicable both to normal electrodes and perm-selective membranes (such as electrolytes in fuel cell).

Figures 9A, 9B:
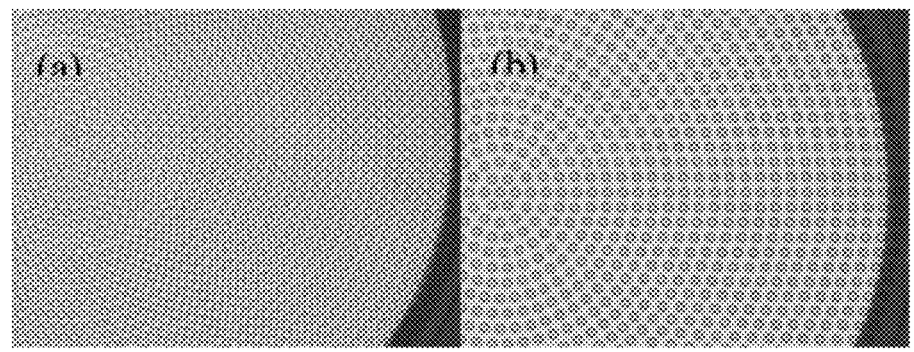
FIGS. 9A and 9B: Close-up (5× magnification) snapshots of micro-pore electrode for pore diameter=20 µm, depth=15 µm and pore center-to-center distance=(A) 30 µm & (B) 40 µm.
Figure 10:
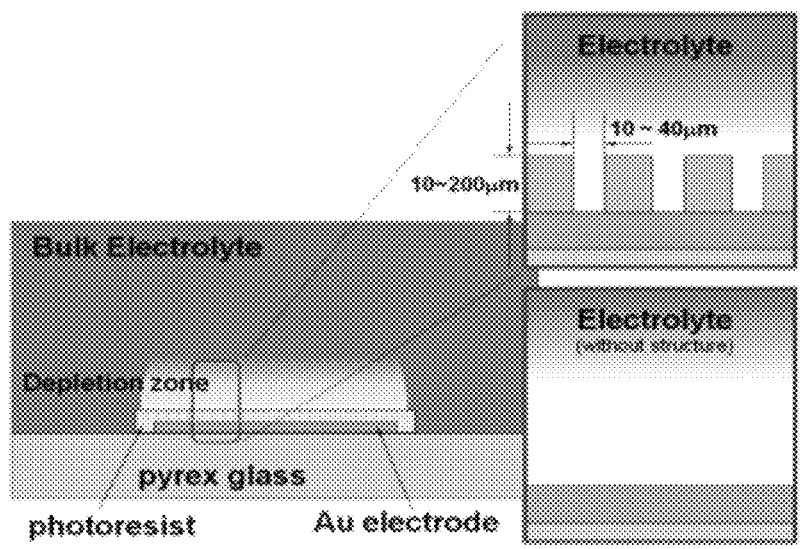
FIG. 10: Schematic of electrode concentration polarization for (a) micro-pore and (b) planar electrodes.
Figure 11:
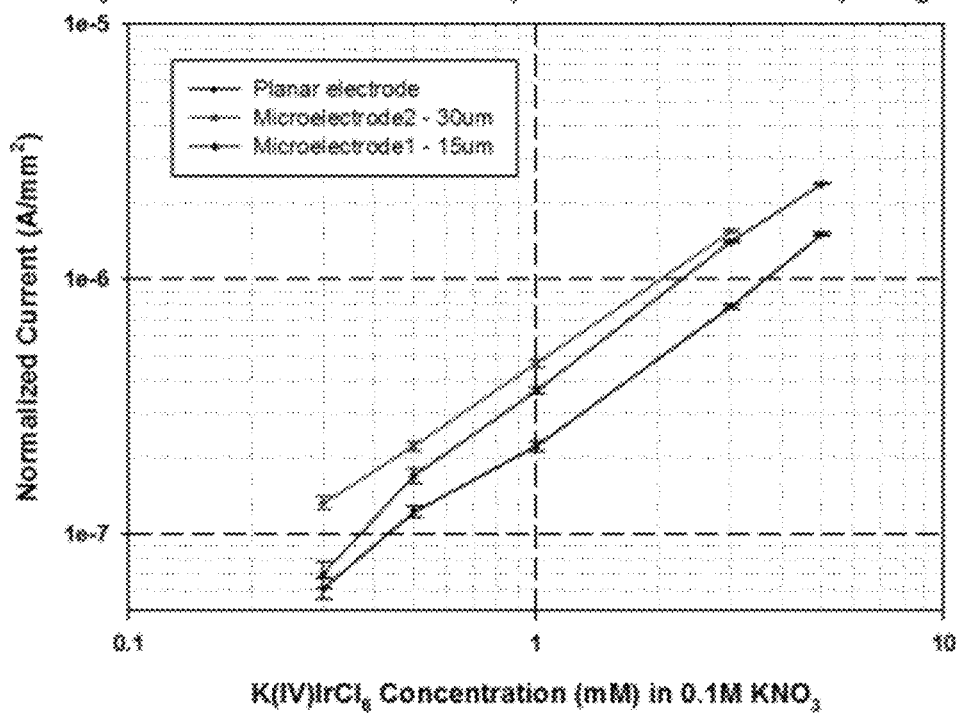
FIG. 11: Normalized steady state current plot with different concentrations of electrolyte. Micropore electrodes specifications are pore diameter=20 µm, center-to-center spacing=30 µm and depth (a)=15 µm denoted as microelectrode 1 and (b)=30 µm denoted as microelectrode 2. The top line of the graph corresponds to microelectrode 2, the middle line corresponds to microelectrode 1 and the bottom line corresponds to the planar electrode.
Figure 12:
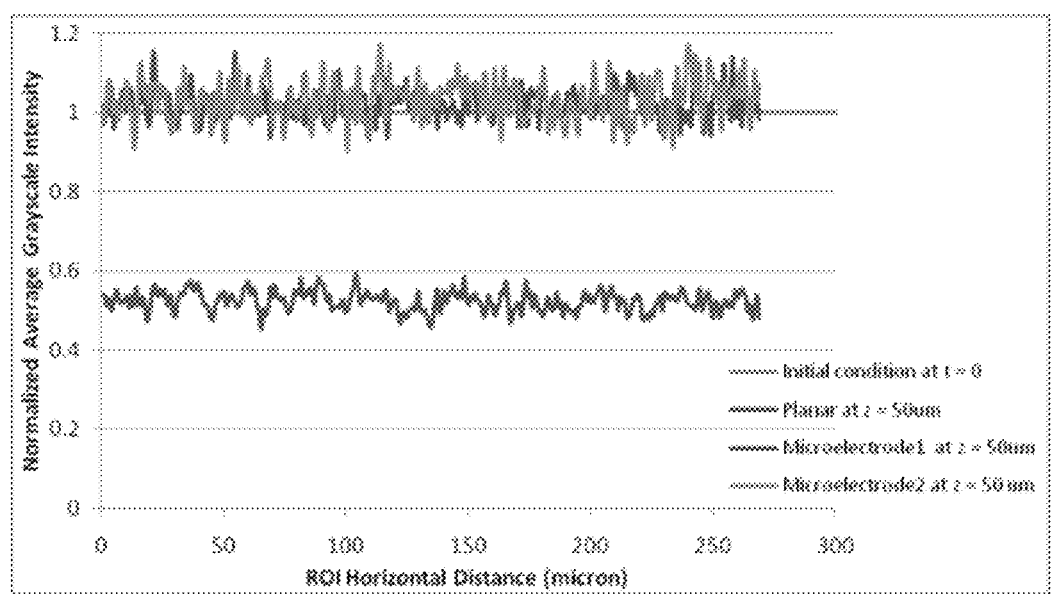
FIG. 12: Normalized average fluorescence intensity plots for different electrodes at a height of z=50 µm w.r.t. Au electrode surface. The small insert presents a typical confocal image with size 1024×1024 pixels and the small red square (region of interest, ROI, is a 270 by 270 µm square) is the post-processing windows for average intensity (y-axis) plot. Fluorescent images was recorded by Zeiss LSM 510 laser scanning confocal microscope. All images were captured at steady state current condition (t>600 s) and normalized respect to its initial conditions at t=0. Working electrolyte for depletion observation is 0.3 mM Potassium (IV) Hexachloroiridate in 0.1 M Potassium Nitride with Alexa Fluor 488 fluorescence in volume ratio of 1/1000. Micropore electrodes specifications are pore diameter=20 µm, center-to-center spacing=30 µm and depth (a)=15 µm denoted as microelectrode 1 and (b)=30 µm denoted as microelectrode 2.

In another embodiment of this invention, non-conducting micro-pore structures were fabricated on top of a planar electrode, as shown in FIG. 8. Commercial photoresist polymer such as SU8 (MicroChem Inc.) with standard lithography process can be used for micro-pore structure fabrication. FIG. 9A-9C shows the micro-pore electrode systems with a pore diameter of 20 μm and center-to-center spacing of 30 μm and 40 μm. This electrode system was similar to a point electrode system in an array formation. As shown in FIG. 10, the micro-pore structure which has a range of size from 10-100 μm for depth, 5-20 μm for pore diameter and 20-50 μm for pore spacing can suppress the growth of ion depletion (or also known as electrode concentration polarization) and contain this depletion thickness relatively much thinner than planar electrode (electrode without structure). The degree of suppression is strongly dependent on the thickness (height) and spacing of the pore structure. The quantitative characterization of steady-state current response for planar and two micro-pore electrodes is presented in FIG. 11. The planar electrode was out-performed by the micro-pore electrodes as shown in FIG. 11 and these results were in good agreement with our earlier hypothesis. For a direct visualization, confocal imaging of fluorescence intensity for different electrodes was recorded and illustrated in FIG. 12. The fluorescence intensity was correlated to the concentration of electro-active species (i.e. ions) for the required electrical current flow in an electrochemical system. The fluorescent images were captured at a height of 50 µm with respect to the electrode surface after 600 s upon the application of voltage for a steady state current flow. In FIG. 12, it was clearly shown that for planar electrode without structure, the fluorescence was depleted to half of its initial concentration at steady state current indicating that the ion depletion thickness was grown beyond 50 µm thick. However, with micro-pore structure the fluorescence concentration remained showing that the ion depletion was successfully suppressed, and hence resulted in a higher current response as shown in FIG. 11.

Overall, these sets of experimental observations and prior studies suggest an emerging picture: Electrochemical efficiency of any electrode (or ion-selective membranes) would critically depend on the spatial extent of the depletion region, which forms a high-resistance barrier to the system.

Figure 13:
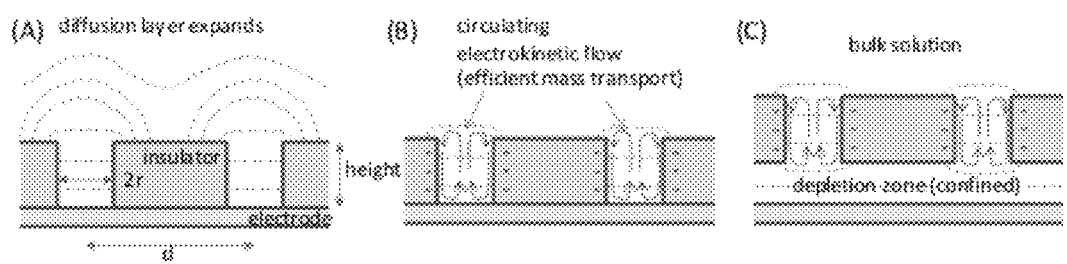
FIGS. 13A-13C: Micro-pore Electrode Arrays (MEA) (A) Traditional Model: in the diffusive model of MEA, enhanced performance of MEA is understood as a result of dissimilar diffusive transport (1D vs. 3D) at the mouth of the 'shallow' recessed electrode hole. (B) our Model: In reality, there will always be an electrokinetic flow (surface-driven, amplified within the depletion zone), which could lead to a fast, circulating flow within the structure. This could significantly enhance the mass transport, and therefore limit the propagation of the electrode polarization. (C) idealized electrode 'silencer' structure: If a fluid restricting structure is placed (without blocking active electrode surface), one could still achieve the same effect of 'arresting' the propagation of depletion zone (concentration polarization), as in MEAs ((A) & (B)). The key difference is that the active surface area of electrode is maintained, therefore achieving the highest net current flowing through the system.

Adding a structural feature (which may be a 'partially blocking' structure (as in FIGS. 13A and B)) would affect the local electrokinetic fluid flow could bring about significant reduction in concentration overpotential (suppression of ion depletion thickness) and enhancement in membrane/electrode performance. In some embodiments, to further boost the performance, some embodiments could be a suspended structural feature (FIG. 13C) without blocking the active electrode surfaces as in micro-pore systems. This could lead to a significant boost in electrode efficiency in various electrochemical energy devices, by addressing the key limitation of the microelectrode arrays (MEA) application to energy applications. The net result of the proposed structure in FIG. 13C would be an additional mechanism to 'arrest' the propagation of depletion region, which will lead to lower concentration overpotential and higher current density.

System Integration

Figure 14:
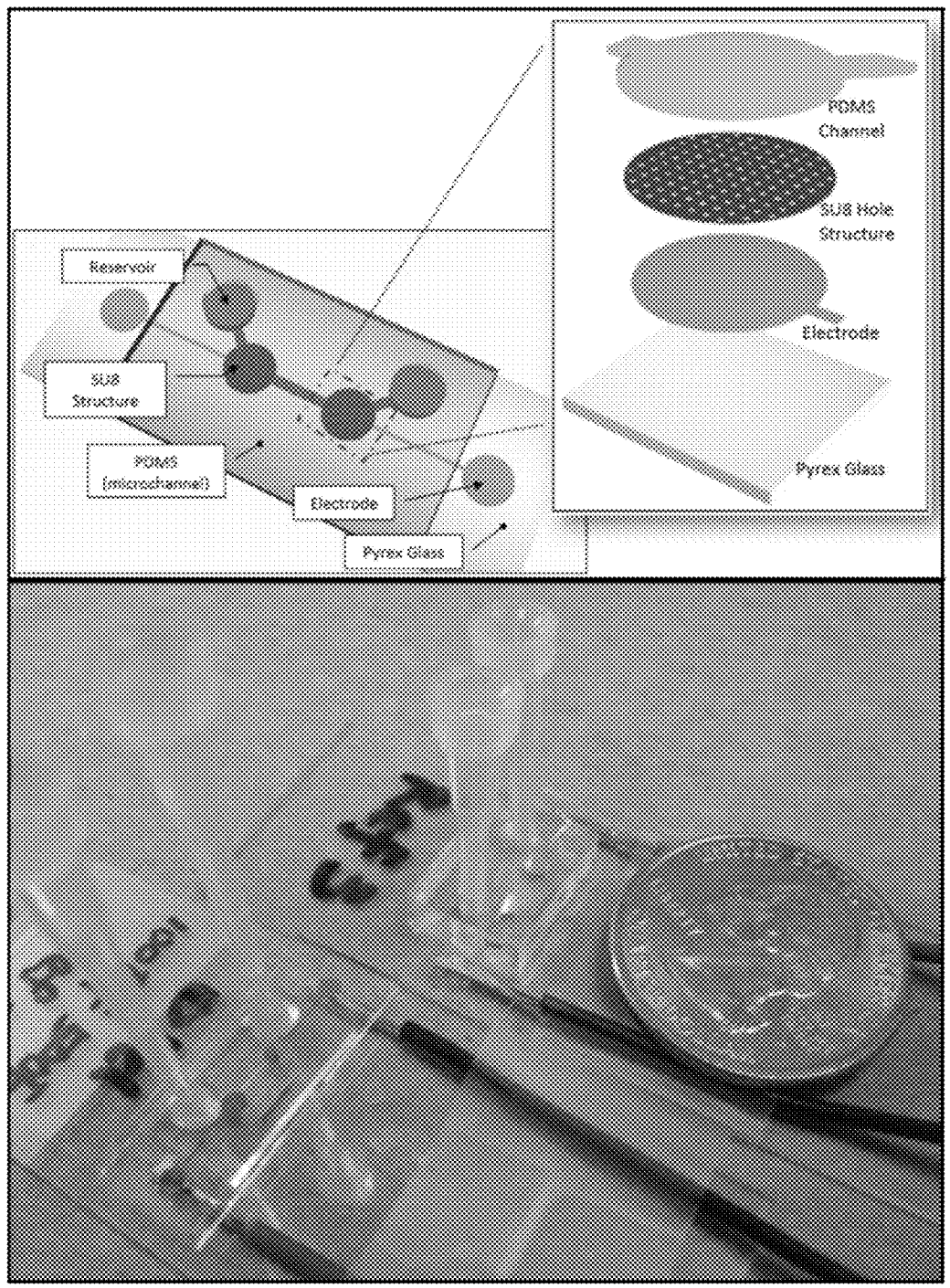
FIG. 14: Simple electrochemical system schematic and snapshot of testing vehicles. Microhole electrode was created by patterning (via photolithography process) SU8 micro-pore structure over Au planar electrode. The test vehicle was completed by covering the electrode pyrex glass with polydimethysiloxane (PDMS) microfluidic channel with a uniform depth of 100 µm. The connecting channel is 500 µm in width and the electrode chamber is dia.=2.2 mm.
Figure 15:
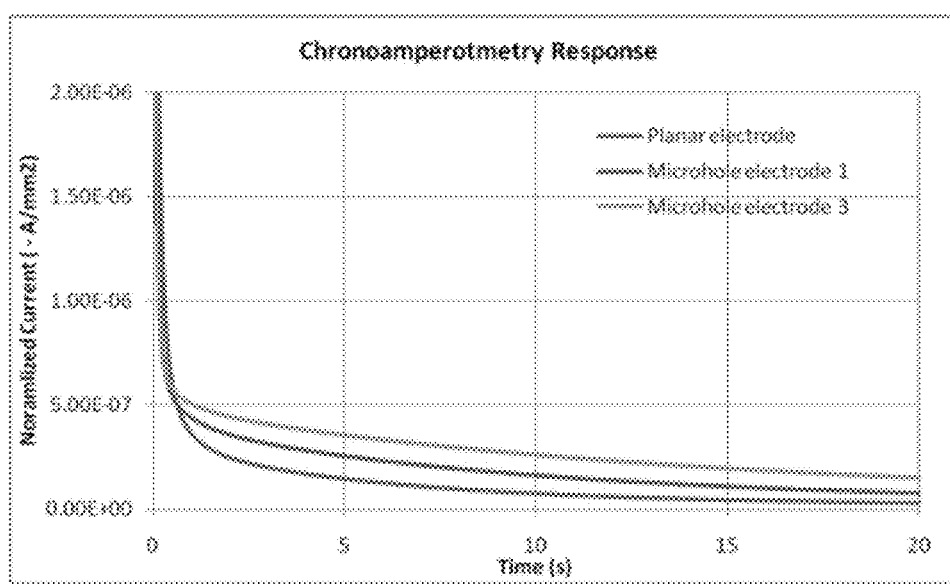
FIG. 15: Chronoamperotmetry responses of different electrode systems for redox reduction process of Potassium (IV) Hexachloroiridate (IV) in 0.1 M Potassium Nitrite. Three different systems were compared: Planar electrode: bare electrode of 1 mm radius, Microhole electrode 1: micro-pore electrodes (1 mm total radius) with r=10 µm, d=30 µm and depth=15 µm, Microhole electrode 3: micro-pore electrodes with r=10 µm, d=40 µm and depth=15 µm. Upon the application of reduction potential, the system current flow decayed as the electrolysis proceeds to deplete the electroactive species near the electrode surface. The net current measurement show that, even though micropore electrode 1&3 has significantly smaller active electrode area than planar electrode, the current reaches the steady states faster and maintains the same or higher net current, in the long run (not shown in the diagram).
Figure 16:
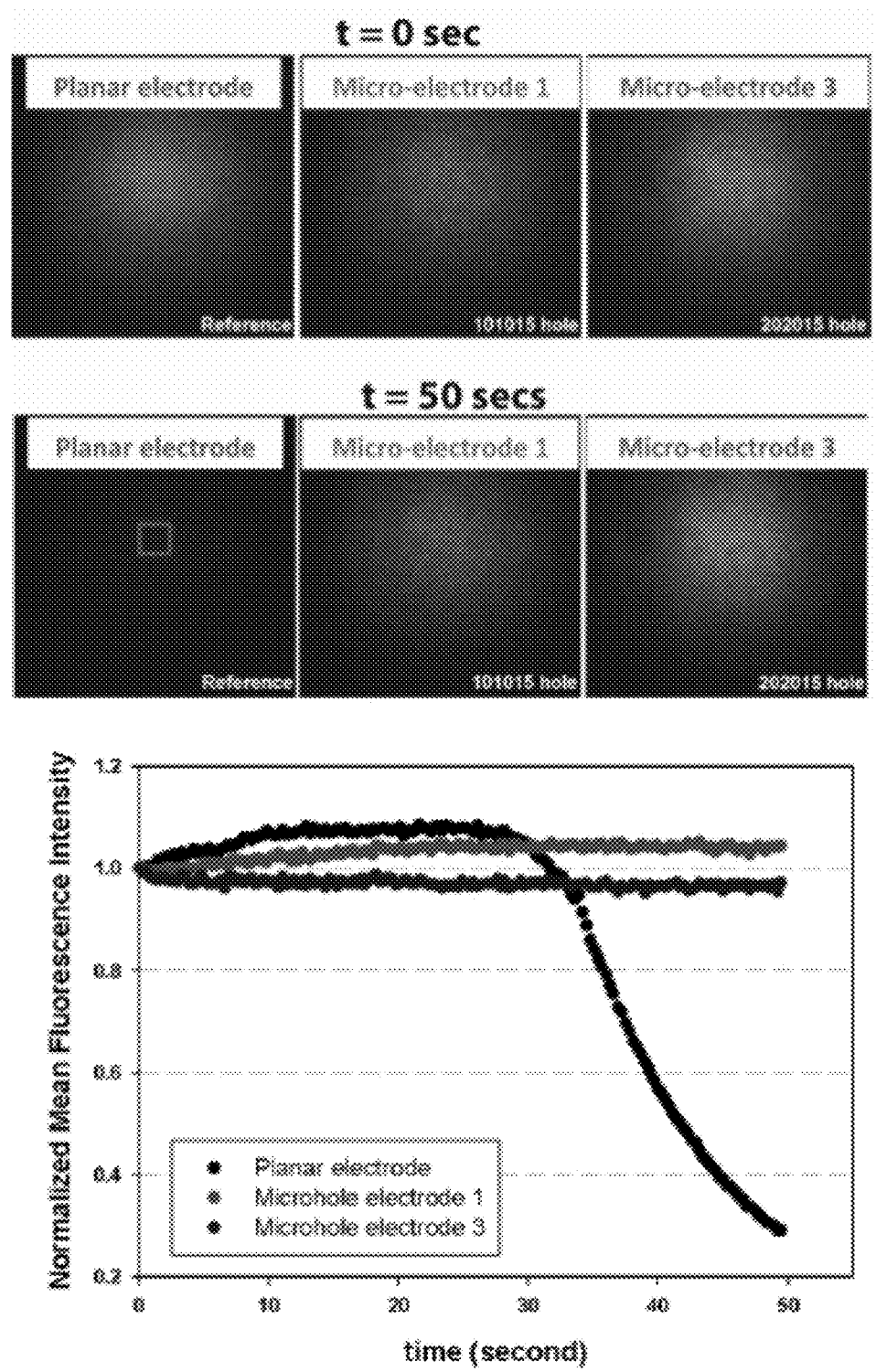
FIG. 16: Two-photon microscopy imaging of fluorescence intensity over a period of 50 seconds upon the application of external applied voltage of 3V. Inserts are the snapshot fluorescent images at t=0 s (top right first three images) and t=50 s (top left last three images). The fluorescence intensity was recorded at a distance of z=50 um w.r.t. Au electrode surface. The two-photon microscopy scanning spot is approx. 2 um in diameter. Small red square on the images represents the post-processing windows for fluorescence intensity analysis. Fluorescence was depleted at around 30 s at planar electrode as it was governed by linear diffusion mechanism, meaning that the depletion layer was expanded without any suppression. Conversely, fluorescence at both micro-pore electrodes was able to sustain over the entire experiment, indicating that the depletion layer has not yet expanded beyond the plane of interest and therefore it could be concluded that depletion layer was well confined. Alexa Fluor 488 fluorescent dye with concentration of 10 uL/mL was used with 1 mM DSP buffer electrolyte. Planar electrode: bare electrode with r=1 mm, Micro-pore electrode 1: r=10 µm, spacing=40 µm and thickness=15 µm, and Micro-pore electrode 3: r=5 µm, spacing=30 µm and thickness=15 µm.
Figure 17A:
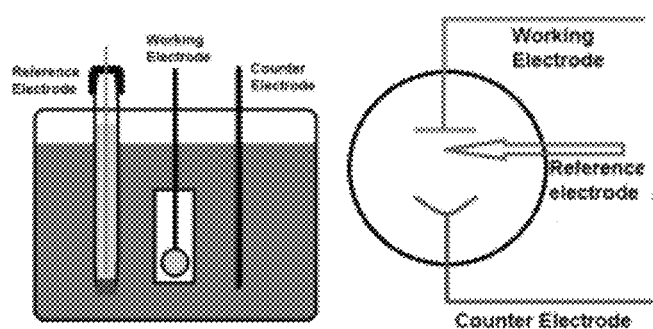
FIGS. 17A and B: (A) Standard electrochemical three electrode measuring system and its electrical connection. This measuring configuration was used in single electrode investigation and (B) Standard two-electrode measuring system connection. This measuring configuration was used in "system integration" investigations.
Figure 17B:
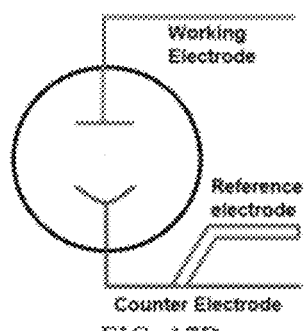

In one example for a system-based performance evaluation, a complete electrochemical system was set-up as shown in FIG. 14. Micro-pore electrodes were fabricated using photolithography process as earlier mentioned and the polymer-based micro-lengthscale channel network structure was fabricated with standard polydimethylsiloxane (PDMS) process. Micro-pore electrode was seated in a cylindrical reservoir located at each side of the system-of-interest (i.e. a microscale connecting channel in FIG. 14). Essentially, it is two disk-shaped micro-pore electrodes connected by a microfluidic channel filled with electrolyte, used for the impedance characterization. In FIGS. 15 & 16, we compared three cases; Planar electrode with no structural features, Microelectrode 1 with a denser array of micro-pores (dia.=10 µm, spacing=30 µm & depth=15 µm), Microelectrode 3 with an array of micro-pores (dia.=10 µm, spacing=40 µm & depth=15 µm). In all three cases, the original size of circular electrodes were the same, but in microelectrodes 1 & 3 an insulating film (SU-8) covers the majority of the electrode surface, creating a micro-pore array systems with relatively high density (low spacing/dia. values). However, the active (open) area of electrode were diminished (to 46% for electrode 1 and 24% for electrode 3, respectively, of the planar electrode) from that of planar electrode system. When we measured the current in the systems in response to a DC bias, we found that the later, quasi-steady-state net current values are quite similar, and at one time point the Microelectrode 3 carries the largest current (FIG. 15). This result can also be correlated to the propagation of diffusion layer (depletion zone) near the electrode, which were directly measured using the two photon microscopy systems (FIG. 16), where it was shown that the depletion region (monitored by dye tracer) were seen to grow more than 50 µm in planar electrode within a minute from the biasing, but not in micro-pore electrode systems.

All chemicals were purchased from Sigma Aldrich and used as received unless otherwise noted.

0.1 M Potassium Nitride ($KNO_3$) supporting electrolyte was prepared by dissolving 5.02 g $KNO_3$ salt in 50 mL deionized (DI) water. While the stock solutions 10 mM Potassium (IV) Hexachloroiridate ($K_2IrCl_6$) in 0.1 M Potassium Nitride ($KNO_3$) were prepared by dissolving 483.1 mg $K_2IrCl_6$ in 100 mL 0.1 M $KNO_3$. Several different dilute $K_2IrCl_6$ (0.1, 0.3, 0.5, 1, 3, 5 mM) solutions were prepared by diluting 10 mM $K_2IrCl_6$ with 0.1 M $KNO_3$ at appropriate ratio.

Cyclic Voltammetry, and Chronoamperometry measurements were performed using a Versastat 3 Potentiostat (V3 Studio Software, Princeton Applied Research) connected with a standard three-electrode cell for single electrode study, see FIG. 1. While a standard two-electrode measuring configuration was used in system integration study, see FIG. 2.

The three measuring electrodes are working electrode, counter electrode and reference electrode (R. S. Rodgers, "Stalking the Wild Potentiostat," *Today's Chemist at Work*, June, 1995, p. 30. (V4#6)). Four different working electrodes were put on test and their surface areas were 3.1416, 1.39, and 0.74 $mm^2$ for planar electrode, microhole electrode 1 & 2 and microhole electrode 3 respectively. [Note: Planar electrode: bare electrode of 1 mm radius, Microhole electrode 1: micro-pore electrodes (1 mm total radius) with r=10 µm, d=30 µm and depth=15 µm, Microhole electrode 2: micro-pore electrodes (1 mm total radius) with r=10 µm, d=30 µm and depth=30 µm and Microhole electrode 3: micro-pore electrodes with r=10 µm, d=40 µm and depth=15 µm.]

A platinum electrode with a large surface area (2.0±0.2 mm in diameter and ~7 cm long) was employed as the counter electrode while the reference was an Ag/AgCl reference electrode (in 3 M NaCl/Saturated AgCl filling solution).

Cyclic voltametry (CV) measurements were recorded between 0.3 and 1 V/Ag/AgCl at several scan rates 10, 50, 100, 500, 1000, 6000 $mVs^{-1}$, while all chronoamperometry (CA) measurements were recorded over a time period of 600 s for a potential step from +0.9 to 0.3 V/Ag/AgCl. The steady current values reported in the text were an average current response of the last 200 s of each CA test. All experiments were carried out in quiescent solutions unless otherwise stated.

While this invention has been particularly shown and described with references to preferred embodiments thereof, it will be understood by those skilled in the art that various changes in form and details may be made therein without departing from the scope of the invention encompassed by the appended claims.

What is claimed is:

1. An electrochemical system comprising a substrate, a plurality of fluidic channels fabricated on said substrate, wherein at least two separate fluidic channels are connected by a junction, wherein at least one part of said substrate contains more than one set of microarrays; wherein said junction comprises an ion-selective membrane.

2. The electrochemical system of claim 1, wherein at least two sets of microchannels are separated by a pillar-free gap.

3. The electrochemical system of claim 2, wherein said gap is between about 25 and 500 μm.

4. A fuel-cell system comprising an electrochemical system according to claim 1.

5. A biosensor comprising an electrochemical system according to claim 1.

6. An electrochemical system according to claim 1 comprising a pillar array wherein the average diameter of pillar is between about 0.1-1000 μm.

7. An electrochemical system according to claim 1 comprising a pore array wherein the average diameter of pore is between about 0.1-500 μm.

8. An electrochemical system according to claim 1 comprising a pore array wherein the pore depth is between about 1-250 μm.

9. An electrochemical system according to claim 1 comprising a pillar array wherein the average pillar height is between about 1-1000 μm.

10. The electrochemical system of claim 1, wherein said ion selective membrane is sulfonated tetrafluoroethylene based fluoropolymer-copolymer.

11. An electrochemical system according to claim 1 comprising a pillar array wherein the average diameter of pillar is between about 1-100 μm.

12. An electrochemical system according to claim 1 comprising a pillar array wherein the average diameter of pillar is between about 5-50 μm.

13. An electrochemical system according to claim 1 comprising a pillar array wherein the average diameter of pillar is between about 5-25 μm.

14. An electrochemical system according to claim 1 comprising a pillar array wherein the average diameter of pillar is between about 7-15 μm.

15. An electrochemical system according to claim 1 comprising a pore array wherein the average diameter of pore is between about 1-50 μm.

16. An electrochemical system according to claim 1 comprising a pore array wherein the average diameter of pore is between about 2-25 μm.

17. An electrochemical system according to claim 1 comprising a pore array wherein the pore depth is between about 2-200 μm.

18. An electrochemical system according to claim 1 comprising a pore array wherein the pore depth is between about 5-100 μm.

19. An electrochemical system according to claim 1 comprising a pillar array wherein the average pillar height is between about 1-500 μm.

20. An electrochemical system according to claim 1 comprising a pillar array wherein the average pillar height is between about 1-250 μm.

21. An electrochemical system according to claim 1 comprising a pillar array wherein the average pillar height is between about 5-100 μm.

22. An electrochemical system according to claim 1 comprising a pillar array wherein the average pillar height is between about 5-50 μm.

23. An electrochemical system according to claim 1 comprising a pillar array wherein the average pillar height is between about 5-25 μam.

24. An electrochemical system comprising a micropore electrode seated in a reservoir, an electrolyte, a substrate, and a support, wherein said substrate comprises one or more microchannels and wherein said micropore electrode comprises an electrode and a micropore array, wherein said micropore array is placed over said electrode.

25. The system of claim 24, wherein the micropore array is fabricated from a photoresist polymer.

26. The system of claim 25, wherein the photoresist polymer is SU8.

27. The system of claim 24, wherein the pore diameter is between about 10 and about 100 μm.

28. The system according to claim 24, wherein the average distance between the pores of said array of micropores is between about 2 and about 100 μm.

29. The system according to claim 24, wherein the depth of each of the pores of said array is between about 10 and about 100 um.

30. The system according to claim 24, wherein the electrochemical system comprises at least two independent sets of micropore arrays.

31. A method of reducing limiting current behavior or reducing convection near an electrode or enhancing electrode performance in an electrochemical system comprising providing an electrochemical system according to claim 24.

* * * * *